US006919959B2

(12) United States Patent
Masten

(10) Patent No.: US 6,919,959 B2
(45) Date of Patent: Jul. 19, 2005

(54) DIGITAL SPECTRAL IDENTIFIER-CONTROLLER AND RELATED METHODS

(75) Inventor: Billy R. Masten, Shallowater, TX (US)

(73) Assignee: Masten Opto-Diagnostics Co., Lubbock, TX (US)

( * ) Notice: Subject to any disclaimer, the term of this patent is extended or adjusted under 35 U.S.C. 154(b) by 286 days.

(21) Appl. No.: 09/849,831

(22) Filed: May 4, 2001

(65) Prior Publication Data

US 2002/0024665 A1 Feb. 28, 2002

Related U.S. Application Data

(63) Continuation-in-part of application No. 09/343,855, filed on Jun. 30, 1999, now abandoned.

(51) Int. Cl.⁷ .................................................. G01J 3/28
(52) U.S. Cl. ....................................................... 356/328
(58) Field of Search .............................. 356/328, 326; 702/28; 382/109, 110

(56) References Cited

U.S. PATENT DOCUMENTS

| | | | | |
|---|---|---|---|---|
| 3,100,204 A | * | 8/1963 | Oberster et al. .......... 250/203.6 |
| 4,206,569 A | | 6/1980 | Randolph | |
| 4,560,275 A | | 12/1985 | Goetz | |
| 4,844,617 A | * | 7/1989 | Kelderman et al. .......... 356/624 |
| 4,968,143 A | * | 11/1990 | Weston ........................ 356/328 |
| 4,996,421 A | | 2/1991 | Rai et al. | |
| 5,134,291 A | | 7/1992 | Ruhl et al. | |
| 5,144,767 A | | 9/1992 | McCloy et al. | |
| 5,296,702 A | | 3/1994 | Beck | |
| 5,329,595 A | * | 7/1994 | Davies ........................ 382/103 |
| 5,389,781 A | | 2/1995 | Beck | |
| 5,394,237 A | * | 2/1995 | Chang et al. ................ 356/328 |
| 5,528,363 A | * | 6/1996 | Fachinger et al. .......... 356/326 |
| 5,585,626 A | | 12/1996 | Beck | |
| 5,606,821 A | | 3/1997 | Sadjadi | |
| 5,717,487 A | * | 2/1998 | Davies ........................ 356/328 |
| 5,763,873 A | | 6/1998 | Beck | |
| 5,774,209 A | * | 6/1998 | Shestock ....................... 356/73 |
| 5,833,603 A | * | 11/1998 | Kovacs et al. ............... 600/317 |
| 5,991,025 A | * | 11/1999 | Wright et al. ................ 356/328 |
| 6,002,479 A | * | 12/1999 | Barwicz et al. ............. 356/326 |

FOREIGN PATENT DOCUMENTS

EP          08361133 A2 *   4/1998
EP          0949490 A1 *   10/1999

OTHER PUBLICATIONS

1997 Annual Report to Cotton Incorporated on the Development of a Robotic Weed Control System for Cotton.
Photograph of Spray Device attached hereto.
B.L. Steward, L. F. Tian, Machine–Vision Weed Density Estimation for Real–time, Ourdoor Lighting Conditions, ASAE Publication vol. 42(6): 1897–1909 1999.
L. tang, L. Tian, B.L. steward, Color Image Segmentation with Genetic Algorithm for In–Field Weed Sensing, ASAE Publication vol. 43(4): 1019–1027 May, 2000.
Precision Chemical Application Systems, Dr. L. Tian, http://www.age.uius.edu/facility/1ft/sprayer.htm.
Precision Farming Sensing Systems, University of Illinois, http://www.age.uiuc.edu/remote–sensing/Sensing.htm.
Proceedings of the SPIE, vol. 3543 Entitled "Precision Agriculture and Biological Quality."

* cited by examiner

Primary Examiner—F. L. Evans
(74) Attorney, Agent, or Firm—Dorsey L. Baker

(57) ABSTRACT

A high speed, low cost, wide spectrum light scanning and sensor unit (10) for receiving reflected light from an object and diffracting the light into segments of wavelengths and a linear sensor array (32) having elements positioned to receive the segments and to measure the relative magnitude of such segments to define a spectral distribution of the object together with a digital identifier-controller (36) connected to said sensing device and having a memory for memorizing a spectral distribution of light representing a first standard object, and additional memory for receiving a spectral distributions of other objects and programmable logic circuitry containing a program for determining the similarity between the standard object and the other objects.

45 Claims, 9 Drawing Sheets

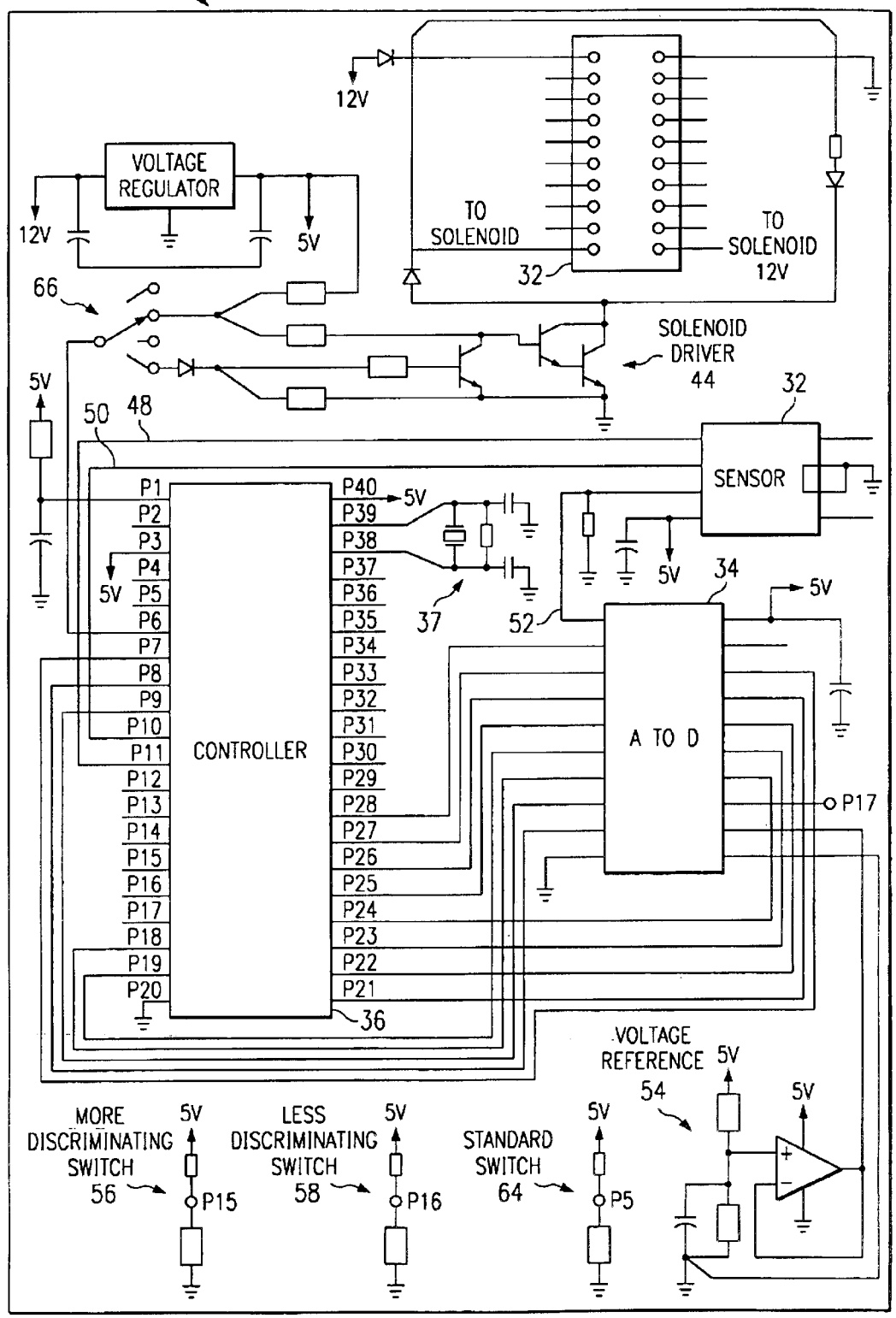

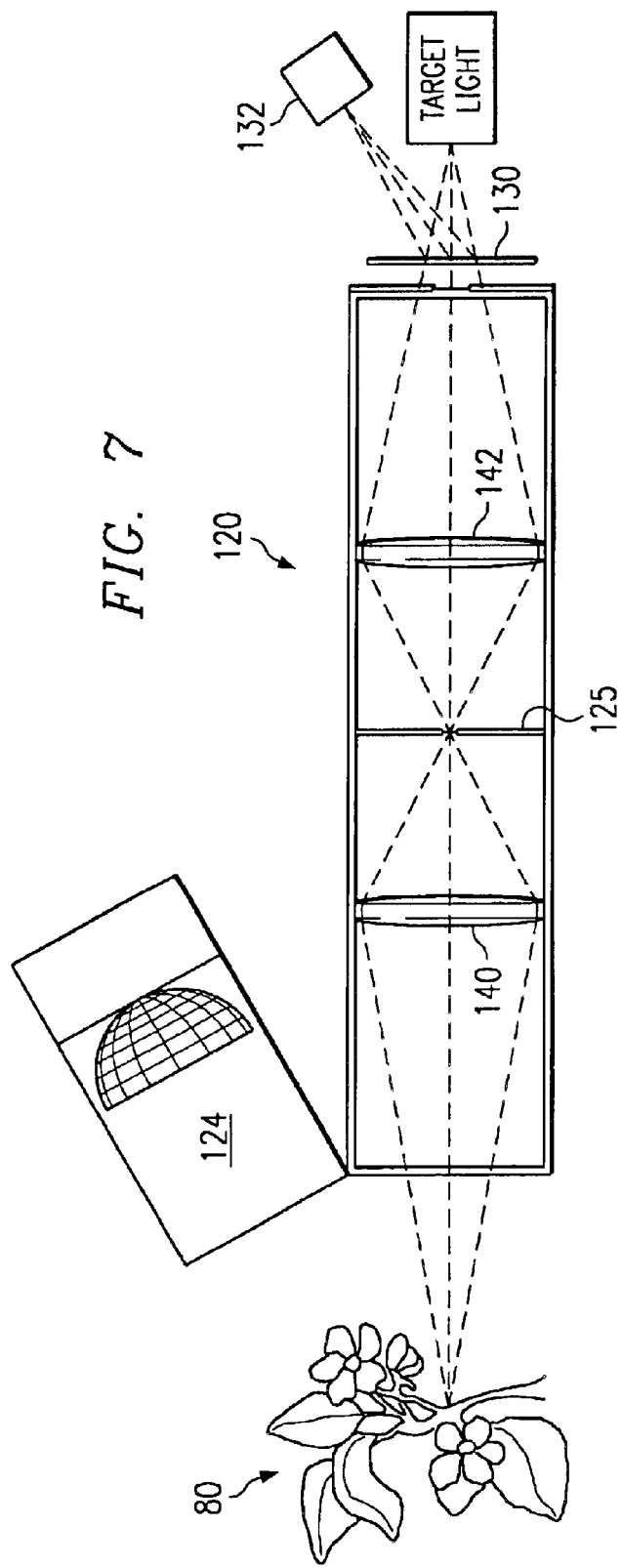

DIGITAL SPECTRAL IDENTIFIER-CONTROLLER AND RELATED METHODS

CROSS REFERENCE TO RELATED APPLICATIONS

This application is a Continuation-in-Part of application, Ser. No. 09/343,855 filed Jun. 30, 1999 now abandoned entitled Digital Spectral Identifier-Controller and Related Methods.

FIELD OF INVENTION

This invention is primarily directed to an electronic apparatus and method for identifying objects and species of objects such as plants in an agricultural field. It includes a wide spectrum light scanning and sensor unit having a digital identifier. More particularly, the preferred embodiment includes an apparatus for selectively identifying 1) all plants, 2) all plants other than agricultural crops 3) specific plants within a field, such as weeds of a specific species.

This invention is also directed to a long recognized problem of selectively applying chemicals to specific plants in a field while avoiding the application of such chemicals to other plants. The practical and economic needs for such a device are substantial. First, if not selectively applied, the herbicide may adversely affect the growing agricultural crop. Second, a substantial portion of a herbicide may be wasted because it is applied to the ground surface and not to the vegetation thus reducing the cost effectiveness of the chemical. Third, application of herbicide to the ground contributes to pollution and long term unknown environmental problems. Fourth, different herbicides have different effects upon different weeds and selective application of the correct herbicide to the proper weeds would achieve the most cost effective eradication.

The plant identification component of my invention may also be combined with a mechanical weed eradicator such that the weeds may be selectively eradicated by a knife, water jet or other tool upon identification of the undesirable plant or weed. In addition, it can be used to selectively apply growth regulators, inhibitors and other chemicals to selected crop plants.

Illustrative of benefits and one field of use of this invention is the identification and spraying of weeds in Roundup® corn or cotton, i.e., plants whose genetics have been altered so as to be unaffected by Roundup® herbicide. Presently, these crops are planted and the Roundup® herbicide is subsequently applied over the entire crop, the ground and weeds of all types. At a recommended application rate of a quart per acre and a cost of approximately $37.50 per gallon, the farmer's total cost of applying the Roundup® herbicide may be $10.00 per acre for each application. Yet, in many fields, less than 10% of this amount of herbicide is needed to kill only the weeds. This invention permits identification of the weeds and limited, but direct application of herbicide to the weeds for a cost savings that may well approach $9.00 per acre in many applications. And clearly, where Monsanto Corporation, the manufacturer of Roundup® herbicides, recommends two or more applications to the Roundup® corn or cotton, this invention will permit substantial savings in the cost of growing these crops.

This invention also applies to the identification of other plants and the application of other chemicals to those plants. For example, growth inhibitors are applied to crops in some years to limit the growth of the plant while simultaneously enhancing the fruit production of the crop. This invention will permit the selective application of the inhibitor to the plant without excess application to the ground and the weeds.

The invention of this application also applies to the field of plant stress and condition analysis. Its capacity to collect wide spectrum light data reflected from a plant enables the use of the invention to quantify the condition of the plant, including the existence of plant stress at a very early stage. More importantly, the invention permits the collection of detail wide spectrum information that cannot be read by the human eye. Such is believed to provide early revelation of the need for fertilizers, moisture, growth inhibitors, or the presence of nematodes and fungi. Importantly, the invention permits an objective method of analyzing plants that avoids subjective and varying interpretations and conclusions that might otherwise result from individual observation.

This invention also has application in other fields such as identification of the condition of plants and objects including fluids and animal tissue. For example, it may be applied to the identification of the ripeness and grading of fruits and vegetables such as tomatoes, quality control of the color of finished objects and the identification of normal, diseased or abnormal tissue in the human body directly or through a scope.

THE PRIOR ART

The prior art has long recognized the problem and need for plant recognition and the application of chemicals only to certain plants. In this decade one popular approach is a spray vehicle having a support bar with seats for three or more laborers holding manually operated spray guns. As the vehicle travels down the rows at a slow speed, the laborers selectively apply a herbicide to any weeds encountered. This is one expensive effort to eliminate the common practice of hoeing weeds in crops such as cotton. In addition to this approach, substantial efforts have been made to develop improved plant identification methods. In large part, the art has focused on the broad identification of vegetation through two basic methods: 1) spatial detection by plant location in the middle of the rows by mechanical means and 2) detection by the use of light such as breaking a light beam or reflection comparison of light beams composed primarily of red and infra-red light wavelengths or of a few wavelengths of light such as the primary colors.

For example, U.S. Pat. No. 4,206,569, which issued in 1978 to Randolph, teaches the detection of undesirable plants by their position between rows of plants. In one embodiment, Randolph teaches the use of a "feeler paddle" to physically feel or sense the position of a plant within the row and to actuate a switch which, in turn, activates a sprayer to apply a herbicide to the plant. In another embodiment, the Randolph patent teaches the use of an infrared light source and sensor to detect the presence of a weed between the rows of plants. Interruption of the infrared light beam indicates the presence of a weed that causes activation of a solenoid valve which applies herbicide to the plant.

U.S. Pat. No. 5,144,767 which issued in 1992 to McCloy et. al. discloses an agricultural sprayer that detects the presence of vegetation by sensing the reflected red and infrared wavelengths and the incident light energy. Subsequently, a CPU determines the ratio of reflected red and infrared light to the incident light, compares them with those of a lookup table that is tailored with values indicative of vegetation. If there is a comparison, then a herbicide spray is applied to the vegetation. McCoy notes that his device identifies green vegetation because it is "quite dissimilar to all other surfaces when analyzing the reflectance values of both wave-bands," i.e., the red and infra-red wave bands.

McCoy does not suggest any capability to distinguish between types of green vegetation, i.e., between weeds of different types or between weeds and crop plants.

Another prior art device is that advertised as the Patchen™ Selective Spray Systems of 101A Cooper Court, Lost Gatos, Calif. 95030, a company that is believed to be a wholly-owned subsidiary of Deere & Company of Moline, Ill. On belief, this unit uses reflections from bursts of light to distinguish between soil and weeds that are spatially located in the middle of the row. A Patchen advertisement states:

"The spray system will spray only weeds, not bare ground. Make No mistake—this is a revolutionary achievement that will deposit dollar savings directly into you bank account."

As far as can be determined, this unit has some ability to distinguish between plants and bare ground, but not between crops and weeds. Neither can it identify specific types of weed. U.S. Pat. Nos. 5,763,873, 5,585,626, 5,389,781 and 5,296,702 are believed to be directed to this device. They represent at least six years of development work in this field.

SUMMARY OF INVENTION

The present inventions are primarily directed to a wide spectrum light scanning and sensor unit having a digital identifier. The preferred application focuses on a low cost plant identifier or recognition system that may be mounted upon a moving vehicle for accurately identifying and distinguishing between different species of plants at conventional agricultural spraying speeds. This identifier may be combined with an apparatus for selectively applying herbicides, plant inhibitors, growth regulators, or selectively actuating a tool such as a knife or water jet for eradicating the plant. Other applications include grading of fruits and vegetables, analysis of plant and animal tissue, etc.

The preferred embodiment of the plant identifier includes an electromagnetic sensing mechanism that is not limited to identification premised upon a few wavelengths of light such as red and infrared. This invention is preferably, an accurate wider spectrum electromagnetic method and apparatus capable of accurately identifying and discriminating between different types of vegetation as well as between vegetation and soil of any type and color.

The invention includes a wide spectrum scanning and sensing unit that having slits through which reflected light is transmitted to a lens and through an associated diffraction grating which separates the light according to its wavelength. The separated light impinges upon a linear sensor array of pixels within the unit which identifies both the relative wavelength and the intensity of the light. Each pixel develops a voltage indicative of the light received. An output is taken from each of the pixels to define the spectral distribution of light reflected by a plant. This spectral distribution defines a "fingerprint" of each species of plant to distinguish one species from another. If desired, the fingerprint can be transferred to and plotted on an oscilloscope (wavelength or pixel location vs. magnitude) for immediate visual examination of the resulting fingerprint of the plant, object or tissue.

This fingerprint or wide spectrum sensing unit also has the capability of identifying the condition of the plants or tissue. For example, it is believed that the spectral distribution will reflect and identify conditions such as plant stress including a lack of moisture, the need for nutrients, the presence of nematodes, etc. To accomplish this function more accurately, it may be desirable to read more pixels from the linear sensor array or to resort to a higher capacity linear sensor array. To accumulate data reflecting a crop condition, this invention may include a transmittal element such as RS 232 port to permit transmission of the spectral distribution of sample plants within a field to a distant receiver or to a portable computer for subsequent, high speed analysis of the condition of the plants.

For plant identification, outputs from the pixel array of the sensing and scanning unit are converted from analog to digital signals and transmitted to a micro controller or comparator which first memorizes the fingerprint of the plants desired to be identified. Thereafter, the tractor and tool bar moves through the crop to generate time interval reflected spectral distributions (frames) of plants within an agricultural crop. These reflected distributions or fingerprints of each frame of other plants are then compared with a memorized spectral distribution of the plant species sought to be identified. If there is a comparison, the identified plant can be sprayed or acted upon in accord with a preset mode.

Preferably, the digital identifier is a micro controller programmed to first memorize a plurality of wavelengths of light reflected by one or more plants to define the "fingerprints" of the plants of interest, to subsequently receive additional reflected wavelengths from other plants in timed intervals as the vehicle moves through the field and to immediately compare the reflected wavelengths to the memorized wavelengths. If the comparison reflects that the received wavelengths are substantially similar to the memorized wavelengths or finger-prints, the plant can be sprayed, not sprayed or eradicated in accord with a selectable program.

Preferably, but not necessarily, the comparison made by this invention comprises a regression analysis to determine the coefficient of correlation between the memorized and the sensed spectral distributions. If there is a high coefficient of correlation, the micro controller emits a signal to treat the plant in accord with programmed instructions, i.e., a solenoid valve may be opened to permit a pump to spray the identified weed or closed so as not to spray the plant, etc. The limit of the coefficient of correlation may be varied to meet any desired certainty of plant identification.

Accordingly, the goals and objectives of this invention are to provide, among other things, 1) a method and apparatus for substantially reducing the cost of applying herbicides to selected or undesirable plants;
2) a method and apparatus for substantially reducing the cost of applying herbicides to selected plant species by identifying plants of the selected species and by applying herbicides only to those species;
3) a method and apparatus of selectively applying chemicals such as herbicides, growth regulators and inhibitors to selected plants rather than to the entire population of plants within a crop field so as to reduce the cost of chemicals and to reduce the possible adverse environmental effects;
4) a very accurate multi-wavelength spectral plant identification and recognition method and apparatus;
5) a method and device for reading, transmitting and accumulating the very accurate fingerprint or spectral distribution of plants for analysis of plant conditions such as stress resulting from lack of moisture and nutrients and the presence of nematodes;
6) a method and apparatus for identification of stress conditions of a plant prior to visual recognition of such conditions by the human eye through the use of a full spectrum fingerprint of the wavelengths reflected by the plant;

7) an apparatus for obtaining objective definitive digital information of the condition of an object or plant which avoids subjective conclusions drawn upon visual personal examinations;

8) a multi-wavelength spectral plant identification and recognition device using a low cost diffraction gratings, and a light sensor array;

9) a low cost, wide spectrum electromagnetic plant identification method and apparatus using a low cost diffraction grating, and a light sensor array and a memory device for storing a fingerprint of the spectral distribution of a plant;

10) a wide spectrum electromagnetic plant identification apparatus and method having the ability to memorize a wide spectrum identification of one plant species and to compare that memorized identification with spectrum identifications of a number of plants so as to identify plants that are similar or substantially similar to the memorized plant species;

11) an accurate plant sensing mechanism with a plant action mechanism so as to selectively apply an action to all identified plants of a particular species;

12) a simple, low cost, minimum maintenance apparatus and method for identifying species of plants or other objects at high speed;

13) a simple, lost cost, minimum maintenance apparatus and method for identifying, grading or selecting objects, plant and animal tissue by their color reflections, 14) a low cost spectroscope and identifier that does not require costly physical calibration;

15) a low cost scanning, sensing and identification unit that can use software for calibration and identification of plants, tissue and other objects;

16) a low cost scanning and sensing device having a target or aiming system to identify the area and object whose spectral image is being generated; and 17) a light scanning and sensor unit having a digital identifier for selectively identifying and evaluating objects, plant and animal tissue of different colors for purposes of evaluation, processing, etc.

DESCRIPTION OF THE DRAWINGS

The manner in which these objectives and other desirable characteristics can be obtained from this invention is explained in the following specification and attached drawings in which:

FIG. 1a is an enlarged perspective view of the preferred plant identifier unit and spray unit of this invention;

FIG. 3 is a circuit diagram of the preferred electronic schematic layout including the micro controller to be used in the apparatus and method for identification of plants;

FIG. 7 is an illustrative, schematic view of an alternative embodiment of the optical scanning and sensor unit having a light beam for aiming at or targeting the plant or object whose spectral image is being scanned.

DETAIL DESCRIPTION

Figure 1:
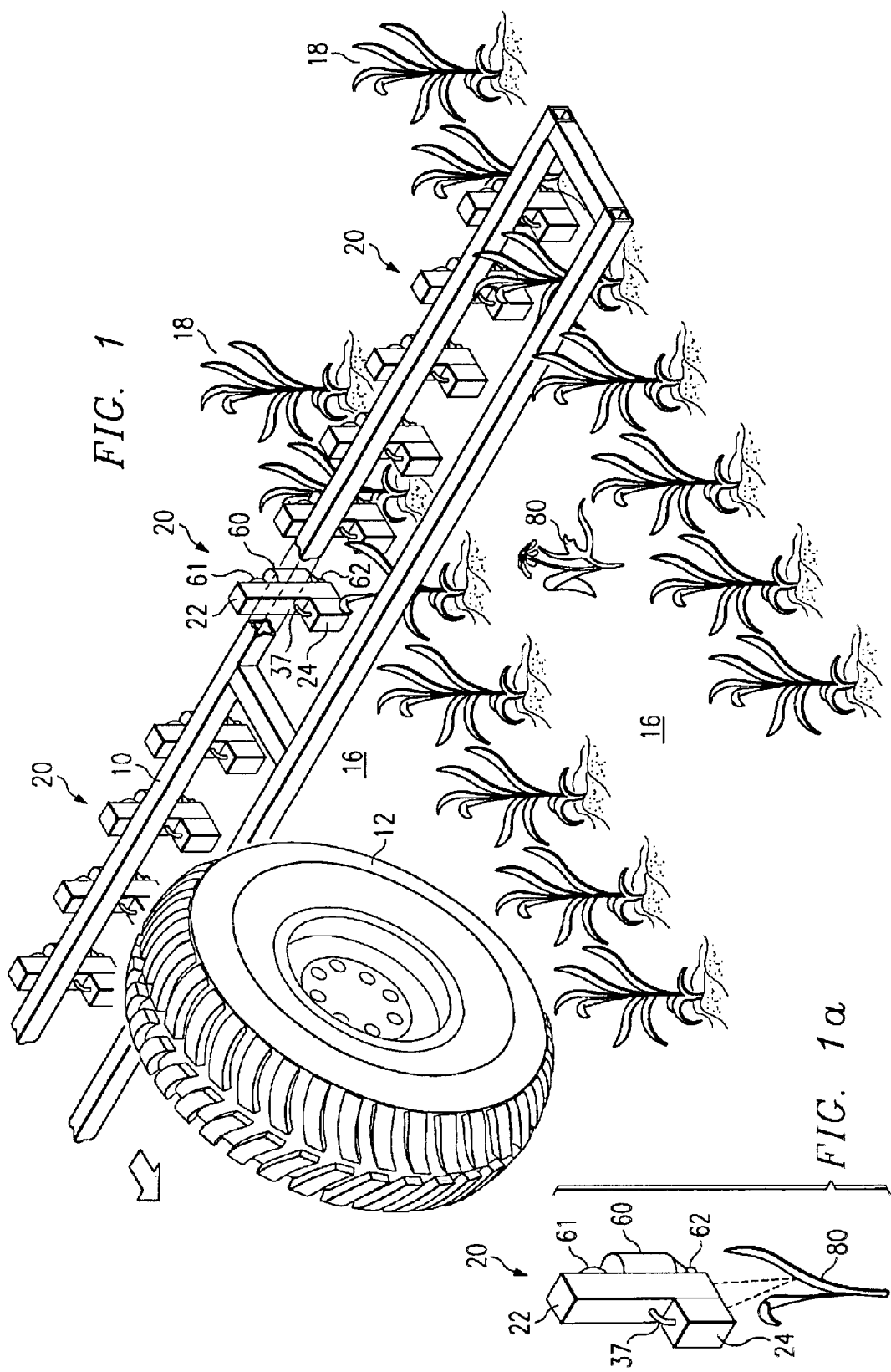
FIG. 1 is a perspective view of a preferred embodiment of the invention depicting the plant identification unit and its association with a solenoid controlling a spray rig, the invention being mounted on the tool bar of a farm tractor.

As depicted in FIG. 1, the preferred embodiment is mounted upon a tool bar 10 that is affixed to a farm tractor whose left rear wheel is shown at 12. This preferred embodiment includes a plurality of plant recognition or scanning and sensor identification units 20. These units may take various arrangements. In the embodiment shown in FIG. 1, these units are positioned side by side and are directed to emit light downwardly and to receive reflections from a row 16. Additional units may be mounted and directed to sense plants on or adjacent the seed bed 18. As will be appreciated, the total number, location and directional mountings of these identification units 20 will be dependent upon the expected size of the plants, the desired accuracy, etc.

In operation, these identification units 20 will travel with the tractor and tool bar 10 down the rows 16 at high speeds of up to 12 miles per hour or more. Consequently, the plant sensing units must scan or take timed plant images (frames) at a very high rate, transmit the images to a comparator or processor to quickly determine if the reflected image is from a plant to which a herbicide or other chemical should be directed. If so, a control or actuation signal is transmitted from a controller to a solenoid 60 to apply a herbicide spray from a pump (not shown) through a nozzle 62 to the plant 80 before the tractor unit has traveled out of spray range of the plant.

The Plant Species Identifier

Figure 2:
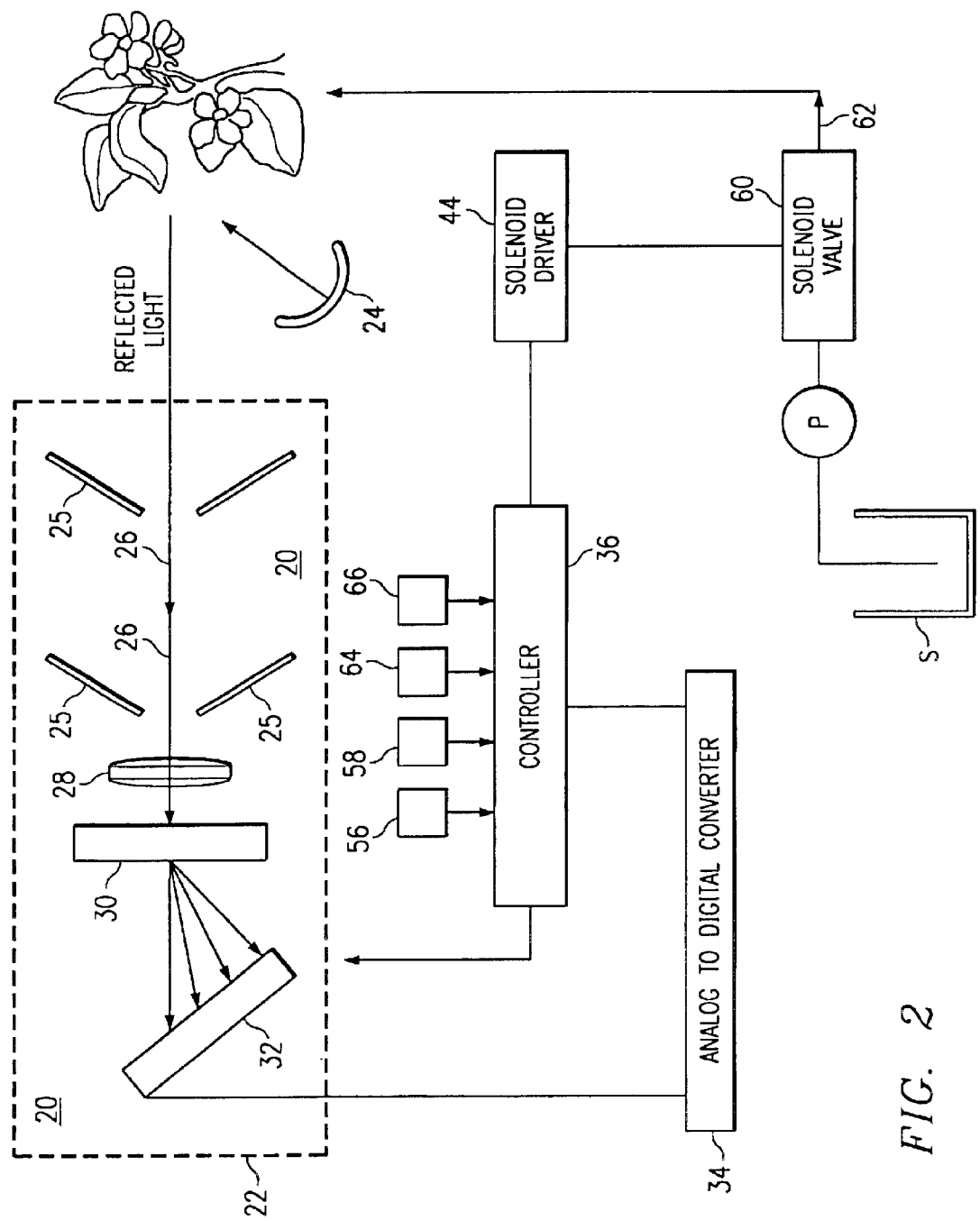
FIG. 2 is a block diagram depicting all of the major components of a preferred embodiment of the plant identifier invention.

FIG. 2 schematically illustrates the design and effective use of the preferred embodiment of this invention for plant identification purposes. After power is applied, the processor initiates its system and program routines. Thereafter, a simple set up is required by the user who must first obtain a "sample" or "standard" species of the plant to be subsequently identified by the invention. A spectral distribution of the light reflected by this "sample" plant is diffracted and placed into the memory of the digital identifier or micro controller 36. An acceptable digital identifier or micro controller capable of serving this function is that manufactured and sold by Motorola, Inc. of Schaumberg, Ill. under the model designation 68HC705C8. This controller 36 has substantial memory and can receive and store a spectral distribution of reflected, discrete wavelengths of reflected light from the plants to be treated. In addition to data memory, it also has program memory and pins to actuate the functions of managing peripheral devices and to carry out the desired comparisons between the digitized fingerprints of the memorized plant species with the reflected fingerprints.

To place the "sample" or "standard" species into the programmed controller, the user or farmer positions the sample of the selected plant in front of a sensing unit 20. Natural or enhanced light from a high intensity lamp 24 is reflected from the plant into the scanning and sensing unit 20 (outlined by dotted lines in FIG. 2). Side plates 25 form slits or vertical apertures 26 to insure that the light is directed through a lens 28 having a focal length, preferably of 1 inch, to a diffraction grating 30. Preferably the diffraction grating has 1,000 lines per meter. This grating 30 breaks the reflected light into discrete wavelengths and directs it to an array of linear arranged sensors 32. Those skilled in the art will appreciate that a prism may be an adequate substitute for the diffraction grating.

The array of sensors may be a TSL 1301 array manufactured and sold by Texas Instruments, Inc. of Dallas, Tex. It includes 102 sensing elements or pixels, each comprising a PN junction. Some or all of the sensing elements may be selected to receive the diffracted light wavelengths and to generate or accumulate, upon inquiry, a voltage charge proportional to the intensity of the received wavelength. To reduce the memory required and for ease of programming, 32 of the 102 pixels have been found to be sufficient for plant identification purposes. This allows for fingerprint definition of the plant comprising 32 different wavelengths and a rather accurate spectral distribution of the plant. Generally, these 32 wavelengths will represent a very wide, if not full spectrum of light extending from about 400 nanometers to about 1100 nanometers. If desired, other sensor arrays could be used to identify shorter or longer wavelengths including infra red lengths.

Figure 4:
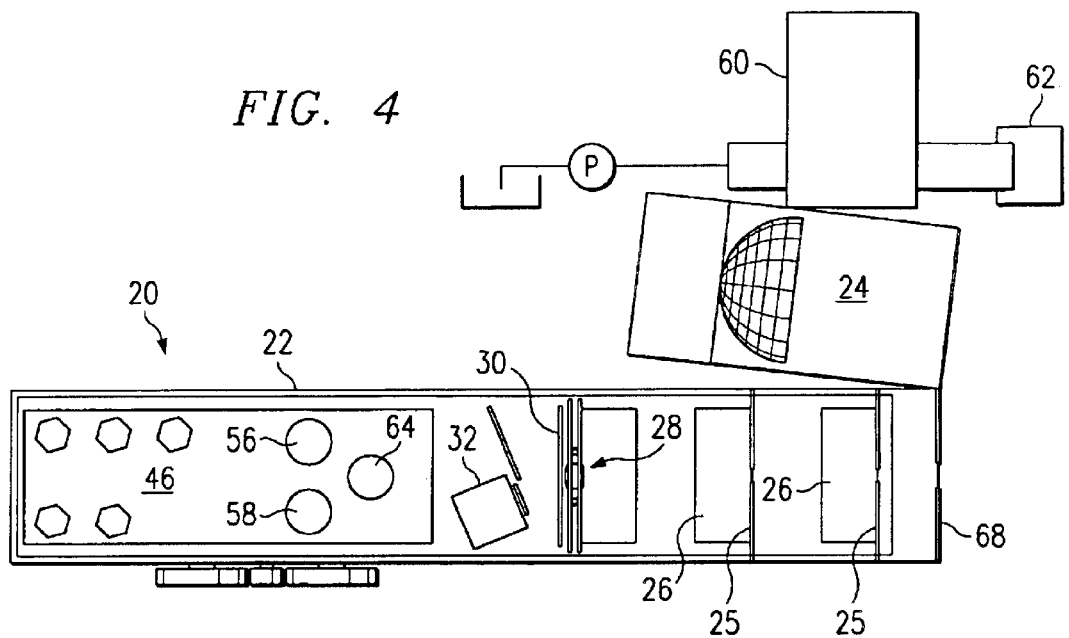
FIG. 4 is an illustrative drawing of a preferred embodiment of the optical scanning and sensor unit.

In operation, each of these pixels develops a voltage that correlates to the quantity of light received. This developed voltage by each pixel can be read by the micro controller 36. For this purpose, controller 36 has a switch 64 (see FIGS. 3 and 4) to enable the farmer to manually instruct the unit to pulse the sensor array 32 to obtain spectral distribution of the "sample" of "standard." This pulse signal will sequentially generate an analog output from all of these pixels to the sensor array 32 and transmit them to an analog-to-digital converter 34. The converter 34 will then direct digital information corresponding to the magnitude of the voltage developed by each pixel into one of 32 memory elements of the micro controller 36 for storage and comparison purposes.

When stored (memorized), the micro controller 36 then has a spectral distribution or "fingerprint" of the wavelengths reflected by the plant to be identified in the subsequent fingerprinting operation in the field. This memorized print thus becomes the "standard" against which subsequent or fingerprints are compared. The spectral distribution of the plant to be identified can also be transmitted to the other sensing units 20 via a serial communication port in the 68HC705C8 micro controller. This port can be tied to the corresponding ports of each light scanning and sensor unit 20 and an appropriate program can be written to allow any one of the units to communicate the spectral distribution of the wavelengths reflected by the plant to each of the other units in the system for ease of set up.

Figure 5:
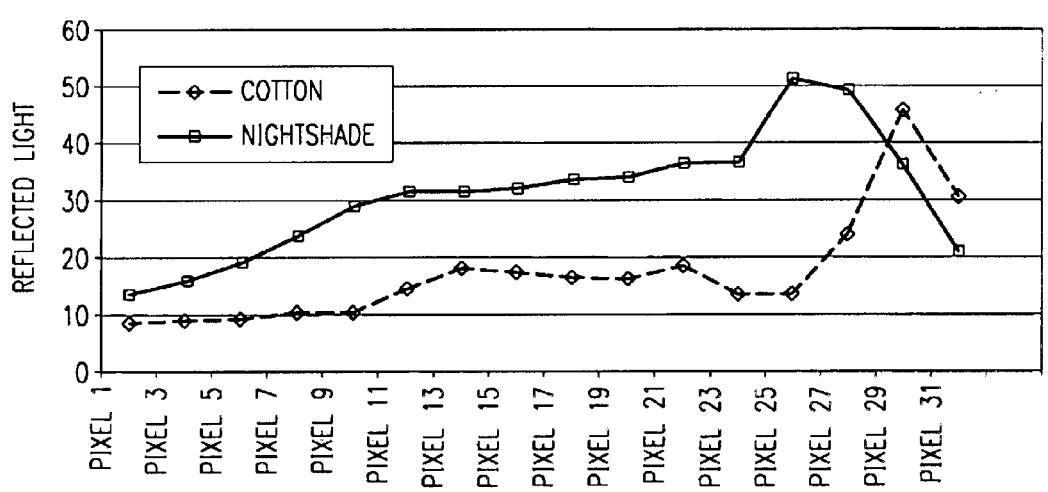
FIG. 5 depicts "fingerprint" graphs of the cotton plant and the night shade weed actually generated by the present invention in which the wavelength (pixel location) of the plant and weed are depicted on the horizontal axis and the magnitude of the reflected light is depicted on the vertical axis to define the spectral distribution of each, (the data points of the wavelengths are estimates since the pixel output was not calibrated by wavelength)

It should be noted that plants to be identified do not have a uniform finger print under all soil, moisture and atmospheric conditions. Thus, the present invention permits the farmer to specifically place in memory the spectral distribution or fingerprint of the plants to be selected for treatment on his farm under the then existing conditions. Such facilitates an accurate plant identification and minimizes error that may result from soil moisture conditions, fertilizers, pests, temperatures, etc. Similarly, the capability of this invention to receive and memorize specific plant fingerprints from the actual farm to be sprayed eliminates the need and costs to develop predetermined fingerprints for dozens of plants. For the first time, such can be done on site. Significantly, an original aspect of this invention is its ability to generate its own fingerprints by directly focusing on the plant, tissue, object or an actual replica or photo representative thereof without the use of prerecorded digital or analog data points. FIG. 5 depicts the spectral distribution or graphical fingerprints of two plants that many farmers would like to identify. One curve reflects the fingerprint of a cotton plant that may be used to avoid application of herbicides or to apply a growth inhibitor. The other curve reflects the fingerprint or spectral distribution of a prevalent, noxious weed, the nightshade in West Texas, these distributions being taken by the present invention. From a comparison of these two curves, it is apparent that they are different and that a regression analysis would generate a very small coefficient of correlation advising of the dissimilarity of the two plants. After the plant, such as the night shade has been fingerprinted by memorizing its wavelength output, the unit is ready to identify all of the plants in a field having the same finger print or "spectral distribution" of wavelengths. This comparison of the spectrum distribution of reflected light from nightshades with that from cotton in FIG. 5 manifests the different fingerprints of these two plants so as to permit their selective identification. It also demonstrates a capability to permit set up and identification of each plant by a sample leaf. Alternatively, the generation of a single fingerprint on an oscilloscope will permit immediate visual identification of the type or condition of the plant or tissue if such is desired.

Assuming that the farmer's decision is to spray all of the plants of the memorized species with a herbicide such as Roundup®, the farmer fills the herbicide reservoir or sump S of FIG. 2 with a proper solution of Roundup®, initiates a pressure buildup by the pressure pump P which is connected to a solenoid valve 60 having a spray tip 62 which is directed at the same area and along the same axis as the scanning unit 20. A solenoid driver 44, controlled by the micro controller 36 activates the solenoid valve 60 to spray the herbicide on the plant.

To insure that the memorized plant is identified and sprayed before the tractor unit passes the plant, the micro controller 36 must first identify the plant as one to be sprayed and then immediately actuate the solenoid valve 60.

To obtain this instantaneous, but very accurate plant identification, the microprocessor 36 is programmed to initialize reading the individual pixels of the linear sensor array 32 preferably at least once every 25 milliseconds. Such has been calculated to permit identification of a plant having a leaf width of approximately 2.5 inch width while traveling at speeds of approximately 5 miles per hour. Thereafter, each clock pulse serially reads the voltage generated by each pixel or sensor to define a spectral image, frame or fingerprint. This voltage is converted to digital information and then stored in other data memory locations of the micro controller 36. After the sensors are read and their output stored in the micro controller 36, the memorized (standard) spectral distribution is compared with the spectral distribution of that reflected by the last plant. While only a few wavelengths could be compared to obtain a reasonably accurate determination of the similarity of the memorized plant distribution with that of the reflected plant, the preferred embodiment of this invention includes programming of the micro controller 36 to run a statistical regression analysis comparing the data points of the spectral distribution or wave chart of the memorized plant with the reflected spectral distribution of each time out-put or frame of the reflected spectral distribution. If the coefficient of correlation between the two distributions is high or greater than the pre-set limit so as to reflect similarity or identity, the micro controller 36 generates an output to the solenoid driver 44 to activate the solenoid valve 60 to apply spray.

Fast acting solenoids such as those sold by Peter Paul Electronics Co. Inc. under the trade mark or model number 32X005806 are sufficient. Spray tips 62 can be selected to apply a very narrow target spray or a wider one depending on the desires of the farmer and the need for accuracy. For example, if one is applying a Roundup® herbicide to nightshade weeds in a Roundup® variety of cotton, some over-spray will not damage the crop and will merely result in a limited over-spray that affects costs and pollution in a limited way. On the other hand, the required coefficient of correlation between the two plant fingerprints may be increased to obtain higher certainty of plant recognition and a finer spray tip can be selected to more accurately direct the herbicide to the identified weed and nothing else. Those acquainted with the art will also recognize that a timing of the activation and duration of the solenoid can be used to actuate the solenoid at a later time or distance so that the solenoid can be activated a fixed distance after the weed is detected thus allowing the spray to take place a fixed distance behind the identification to avoid contaminating the optical system with chemical. If the solenoid is of a type to be deactivated, then the program of the micro controller can include such a function.

It should be appreciated that the micro controller 36 must be very fast and should read the memorized images and run a regression analysis numerous times per second to insure that each weed or plant is scanned for its spectral distribution and considered for spray by the regression analysis.

FIG. 3 depicts an electronic circuit board design 46 that has been demonstrated to be effective for the purposes of this invention. The controller or digital identifier 36 is located on the left side of the board 46. Leads 48 and 50 prepare (SI) and initiating (CLK) data communication of the analog magnitude contained in each of the sensors of the array 32. This accumulated data is communicated to the analog-to-digital converter 34 via lead 52. The analog to digital converter 34 converts the analog signal to a binary digital signal and delivers the result to port C, i.e., pins 21 to 28 or (PC0 through PC7), of the micro-controller 36. A timer built into the micro-controller 36 repeatedly generates a clock pulse to take a new fingerprint of its visual area and deliver the fingerprint or spectral distribution in binary form to the micro-controller 36.

The reference circuit 54 at the lower right of FIG. 3 supplies an upper reference for the analog to digital converter. This is set to the highest expected value of the analog output signal 52.

After each time interval light data is fed into the micro controller 36, it runs a preprogrammed regression analysis to determine the coefficient of correlation between the spectral distribution of the memorized plant and the spectral distribution of the plant of the new time interval frame. If the coefficient of correlation is equal to or greater than a predetermined value, the micro controller emits a signal through the solenoid driver 44 to activate the solenoid 60 to spray identified nightshade plant. Preferably the result of the correlation computation is converted to an integer factor that is representative of the coefficient of correlation so as to simplify the spray decision and avoid a decimal number.

The pre-set value or correlation limit established for actuation of the solenoid driver 44 can be increased as desired through discriminating switches 56 and 58. The non-grounded side of the more discriminating switch 56 is connected to pin 15 of the micro-controller 36. When this pin is activated, the program in the controller increases the limit of the correlation coefficient by $1/256$. When pin 16 of the micro-controller is activated by pressing the less discriminating switch 58 the correlation coefficient limit is decreased by $1/256$. The increment value, $1/256$, may be decreased by a software change for greater accuracy.

A standard switch 64 may be used to instruct the micro controller 36 to memorize the spectral sample (or standard distribution) in a specified portion of its memory to be used in subsequent calculations of the correlation coefficient or its factor. This allows the unit to spray only things that are like the sample or only things that are not like the sample. As those skilled in the art will appreciate, an alternative method of accomplishing this task would be the use of switches connected to a micro controller pin and software to change the logic mode. For example, instead of identifying plants to be sprayed with a herbicide, the invention can be set up to identify the planted or money crop—and use an inverter to spray all other vegetation. Thus, the mode switch 66 can be used to change from the mode that actuates the solenoid 60 (FIG. 4) when the correlation coefficient limit is exceeded to a mode where the solenoid 60 is deactivated when the correlation coefficient limit is exceeded.

Figure 2A:
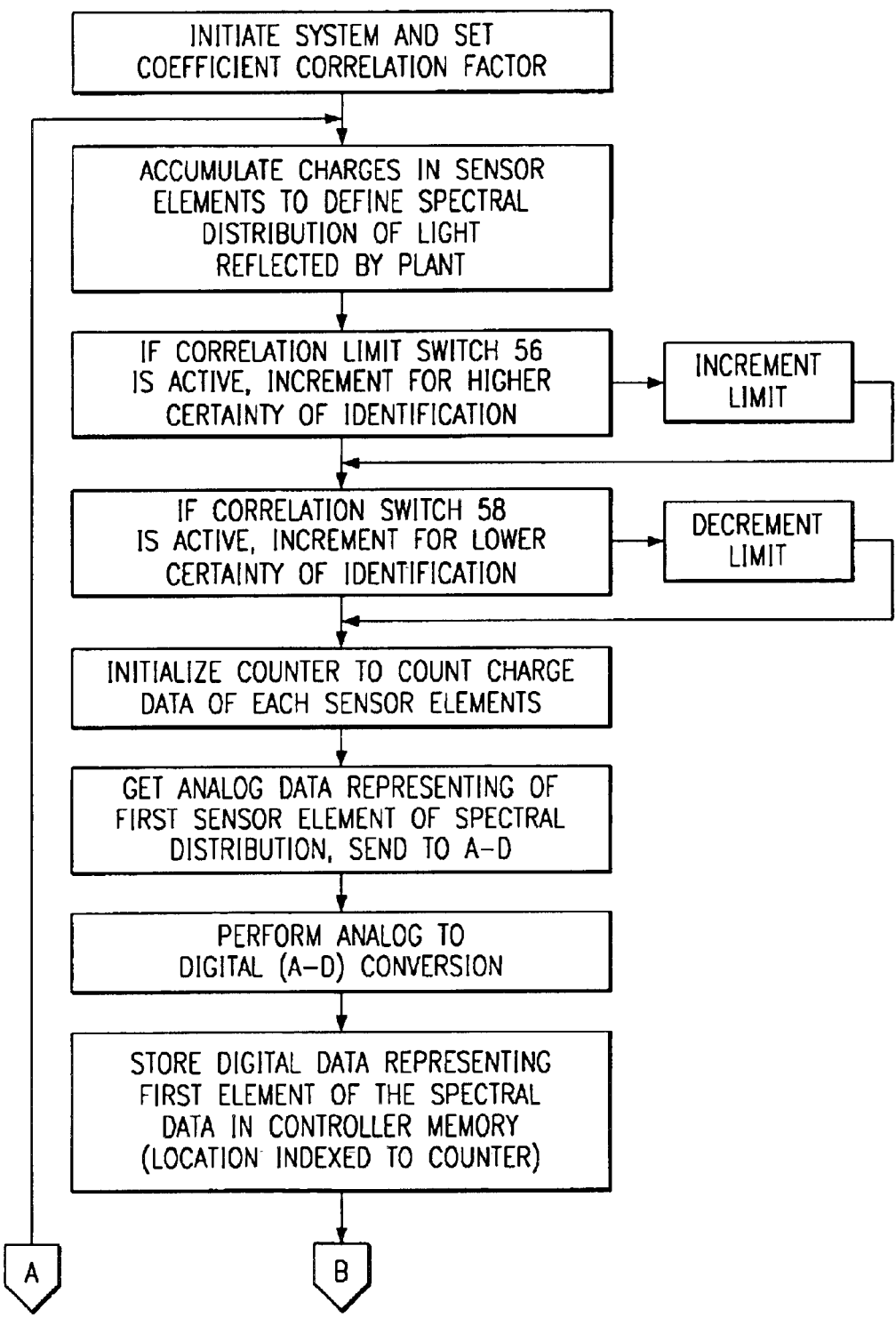
FIG. 2(a) is a chart depicting the functions of the software to be incorporated into the microprocessor.
Figure 2B:
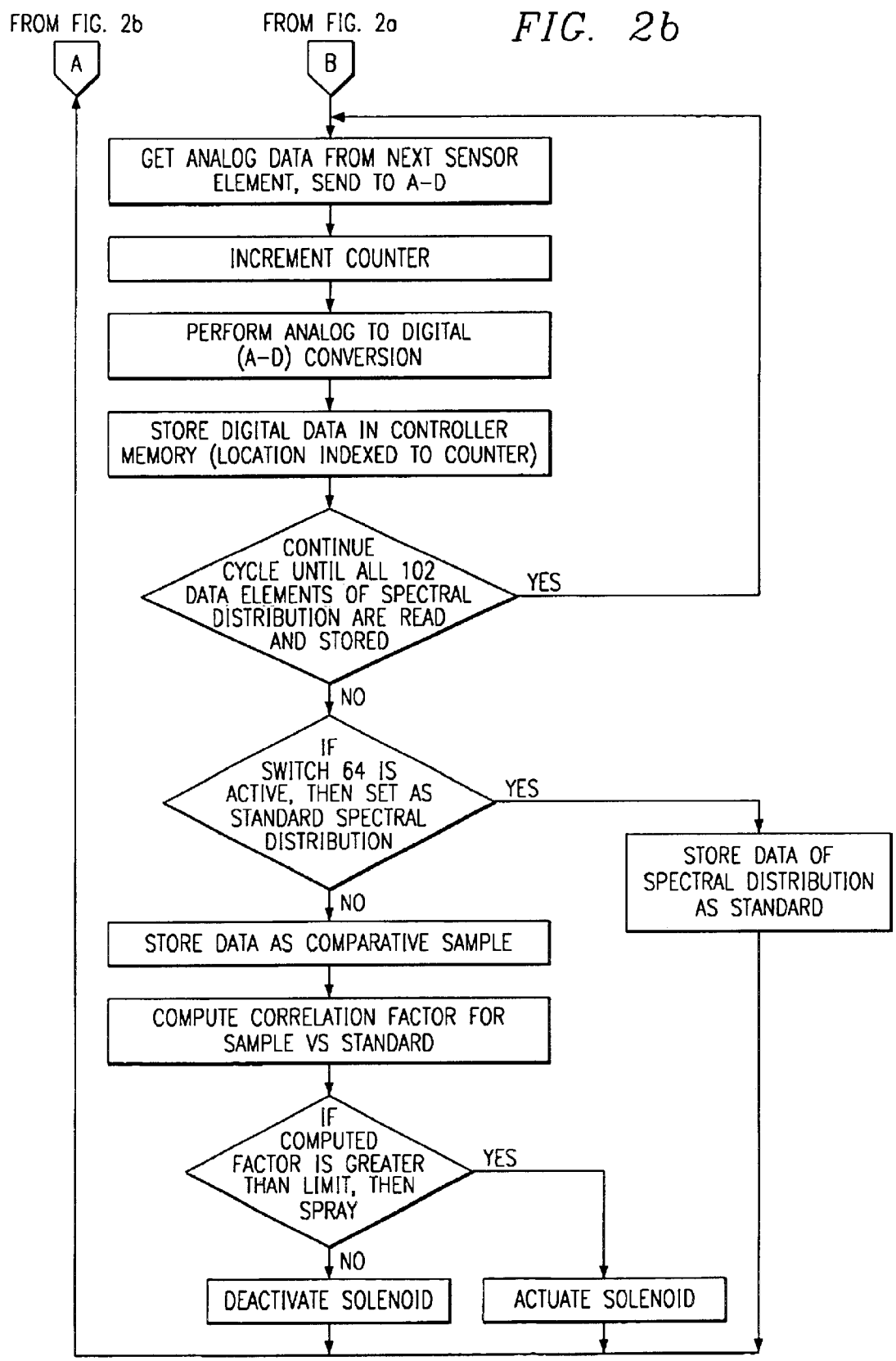
FIG. 2(b) is a continuation of the chart of FIG. 2(a)

To facilitate one's understanding of this invention, the flow chart of FIG. 2(a) further discloses the functions of the software of the micro controller 36 as described herein. In addition, these functions have been incorporated into the following machine code for the identified Motorola micro controller MC68HC705C8 in a manner to utilize 32 pixels of the light sensor array so as to 1) effectively memorize a spectral distribution of a sample plant, 2) to subsequently take spectral distributions (fingerprints) of other plants, 3) to compare those plants with the sample, and 4) to identify the other plants that are of the same species or spectral distribution as the sample.

Machine Code

S1130100A620B777A60FB7BBA600B7BFC61FDFAA46
S113011082C71FDFA6A7B704A600B706A6E7B705E0
S11301203F02A690B7BBCD044ECD0169CD01840D2D
S1130130000BA600B7BFB778B7BDCC0141A601B785
S1130140BFCD045D00BF022000CD04D9CD04C0CDD5
S1130150019FCD01CECD01FDCD022D1B00BE42B3CA
S11301607725O3CD04F2CC0126060115003B1410BB
S11301703BB677AB01B777A1402508A640B77720F7
S113018002113B81080115023B14123BB677A00112
S1130190B777A1012208A601B7772002133B81A6F5
S11301A000B7B5B7B4B7B3BFBCAE425CA363271DF9
S11301B0BFB6F6FECD0504BBB5B7B5BFBEB6BEB976
S11301C0B4B7B4A600B9B3B7B3BEB620DE81A600F7
S11301D0B7B2B7B1B7B0BFBCAE785CA399271DBFA7
S11301E0B6F6FECD0504BBB2B7B2BFBEB6BEB9B15A

```
S11301F0B7B1A600B9B0B7B0BEB620DE81A600B7CD
S113020036B737B738BFBCAE425CA363271EBFB650
S1130210F6EE36CD0504BB36B736BFBEB6BEB9372B
S1130220B737A600B938B738BEB620DD81B638B7BF
S11302303FB637B740B636B741CD0555B63FB738A8
S1130240B640B737B641B736B6B9B740B6BAB74114
S1130250A600B73FCD0555B640B7B9B641B7BAB653
S1130260B7B740B6B8B741A600B73FCD0555B640BD
S1130270B7B7B641B7B8B6B7B73DB6B8B73EA6003C
S1130280B73CB6B9B740B6BAB741A600B73FCD053B
S113029031B636B03EB7362410B637A001B737248E
S11302A008B638A001251AB738B637B03DB7372499
S11302B008B638A001250AB738B638B03FB7382495
S11302C008A600B736B737B73898B636B7ACB637DE
S11302D0B7ABB638B7AAB6ABB740B73DB6ACB741C3
S11302E0B73ECD0531B63CB739B63FB7AAB63DB730
S11302F0ABB63EB7ACAE045A270B39AC39AB39AA0E
S11303003939CC02F7B6B3B73FB6B4B740B6B5B7D0
S113031041CD0555B63FB7ADB640B7AEB641B7AF60
S1130320A600B73FB73CB6B7B740B73DB6B8B7417C
S1130330B73ECD0531B6AFB03EB7AF240EB6AEA0D2
S113034001B7AE2406B6ADA001B7ADB6AEB03DB7A9
S1130350AE2406B6ADA001B7ADB6ADB03FB7ADB6ED
S1130360B0B73FB6B1B740B6B2B741CD0555B63F09
S1130370B776B640B775B641B774A600B73FB73C79
S1130380B6B9B740B73DB6BAB741B73ECD0531B6F9
S113039074B03EB774240EB675A001B7752406B6C2
S11303A076A001B776B675B03DB7752406B676A0CB
S11303B001B776B676B03FB776B6AEB73DB6AFB74F
S11303C03EB674B741B675B740CD0531B63CB73AC1
S11303D0B63FB7ADB63DB7AEB63EB7AFAE045A27DB
S11303E00B363A36AD36AE36AFCC03DEAE505A27B6
S11303F054B6ACB0AFB7AC241BB6ABA001B7AB24BA
S113040013B6AAA001B7AA240BB639A001B73924A0
S113041003CC0445B6ABB0AEB7AB2413B6AAA00167
S1130420B7AA240BB639A001B7392403CC0445B6C6
S1130430AAB0ADB7AA240BB639A001B7392403CCAE
S11304400445CC03EEBFBEA650B0BEB74281BFBCCC
S1130450BEBB9D9D9D9D9D5A26F8BEBC81AE415C50
S113046010001200110013 00CC04821200130012B9
S11304700013001200130000BF022003CD048CCD32
S113048004A05CA36526E412001300811E011A0176
S113049014001C011B0115001F011E01B602F78187
S11304A0BFBCB6BCAB36B7BEBEBE1E011A0114003B
S11304B011C01B0115001F011E01B602F7BEBC8101
S11304C03FBA3FB94F98AE79FB25085CA39926F84B
S11304D0B7BA813CB99820F3813FB83FB74F98AE83
S11304E043FB25085CA36326F8B7B8813CB7982082
S11304F0F3811A00B6BBB7BEA622B7BBCD044EB675
S1130500BEB7BB813F343F35B732A609B730B632E8
S11305103A3027022003CC052C383539345824F0DE
S1130520B732BB3524023C34B73520E2BE34B6358D
S113053081AE103F3C3F3F363D363E240CB63FBBB8
S113054041B73FB63CB940B73C363C363F363D3602
S11305503E5A26E78198AE065A2709363F3640367A
S1130560419820F481B63FB73CB640B73DB641B799
S11305703E393E393D393CB641BB3EB73EB640B943
S11305803DB73DB63FB93CB73C81AE253F763F759C
S11305903F745A2710363C363D363E25022003CDA3
S11305A005A6CC059281B674B941B774B675A90095
S11305B0B775B676A900B675B940B775B676A90011
S11305C0B776B93FB77639413940393F81CC01001C
S10805D08080808080A2
S10F1FF405D405D305D205D105D005CDD8
S9030000FC
```

FIG. 4 depicts one mechanical arrangement for the scanning and sensor unit 20. As shown, each entire light scanning and sensor unit 20 is contained in a housing 22 that is formed of rectangular tubular stock. To the rear of the sensor unit 20 is mounted the circuit board 46. A light source 24, preferably Sylvania lamp MR 6 is affixed in similar tubular stock adjacent the housing 22. Light is reflected from an object to the right and is reflected through the shield 68 and apertures 26, through lens 28 and diffraction grating 30 which diffracts the light the longer wavelengths through a larger angle than the shorter ones. The result is a rainbow of light on sensor array 32 with infrared to the bottom and ultraviolet at the top and all parts of the visible electromagnetic spectrum in between.

Alternative Embodiments, Modes and Methods

Persons skilled in the art will appreciate that the disclosed scanning and identification invention can be utilized in several ways and is not limited to a specific mode. As earlier mentioned, a mode switch 66 can be used to control the output of the micro controller so that it sprays the vegetation having a high correlation coefficient to the sample, or so that it does not spray that vegetation. In addition, the planted crop can be fingerprinted, identified and sprayed with growth inhibitors, etc. rather than herbicides. Another alternative mode of operation of this invention can be obtained by placing the fingerprint of two or more samples of plant species into memory, and programming the micro controller to run two or more comparisons or regression analysis before issuing a determination to actuate the sprayer or other device. This mode and modification can take several forms. For example, if a farmer desires to spray two weeds with different herbicides, he could associate one regression analysis with one solenoid driver and herbicide sprayer and a second regression analysis with another solenoid driver and herbicide sprayer. Such is a desirable capability when different herbicides have different effectiveness on different plants. In addition, the farmer might hold a soil sample under the sensor unit and place its spectral distribution in memory. Should the comparator then determine that the compared time interval spectral distribution is the same as that of the memorized soil sample, the microprocessor can be programmed not to spray. This mode would permit the spraying all vegetation, but not the bare ground.

In addition to the soil sample spectral analysis, a farmer might store a second distribution of the cotton plant of FIG. 5. After the microprocessor runs a regression analysis comparing the reflected distribution with each of the soil and cotton plant distributions, it can easily be programmed or provided with a separate logic board to activate the sprayer only if neither cotton nor soil is detected.

Those skilled in the art will also appreciate, that rather than using a single micro controller 36 to memorize two or more plant or soil spectral distributions, one might use two or three units and focus them on the same frame or image. Each unit could memorize a single distribution and identify a single object or plant species. The output of these separate devices could be input to a logic board with switches that would permit any of the commonly known logic decisions such as those of AND, NAND, OR, NOT etc. logic gates. In addition, the present invention can take many forms and utilize numerous components that perform in substantially the same way to achieve substantially the same result. For example, numerous controllers or digital identifiers could be used in lieu of the Motorola controller disclosed in this specification. Those skilled in the art will appreciate that the essential functions of the digital identifier or controller 36 are those of providing memory for the storage of the spectrum data and of the program steps reflecting the desired functions as well as logic circuitry having the ability to perform the desired functions and comparison. Such may take the form of an arithmatic logic unit or its equivalent. In addition, the digital identifier should have an Input/Output (I/O) capacity to receive data from the sensor array and to control at least one peripheral device such as the sensor array 20. Preferably, the identifier will have input and output pins to activate the solenoid and to receive the data reflecting the spectral distribution or to transmit the information. Consequently, any of the various micro controllers, computers, microprocessors and digital signal processors (DSP) which have the necessary components will be acceptable alternatives. Alternatively these individual devices such as the memory and I/O devices can be purchased separately and wired together to accomplish the necessary functions.

More specifically, one alternative is a Digital Signal Processor (DSP) Model No TM320F240 which is made and sold by Texas Instruments of Dallas, Tex. In addition, Model No. TMS 320F243 has the capabilities to meet the requirements of this invention. These units provide enhanced features such as high speed (20 megahertz), additional storage and the ability to point to two sets of data simultaneously. In addition to the use of alternative processors, those skilled in the art will appreciate that different lamps may be utilized and that in many cases, the lamp will not be necessary with natural light being sufficient. Too, alternative array devices that are more sensitive or have different pixel counts may be utilized instead of the TSL 1301. For example, TSL 1401 from Texas Instruments, Inc. of Dallas, Tex. will permit the collection of 128 wavelength sectors rather than 102. And though the invention preferably uses a regression analysis to develop a coefficient of correlation, the invention may well provide the desired accuracy of plant identification by merely comparing only three or four data points of the light spectrum. This could be accomplished by use of 3 or 4 discrete sensors properly located to sense the desired wavelengths of light and a simple comparison program that does not require a regression analysis or computation of the coefficient of correlation. A multiplicity of linear arrays or an area array, could be used to reduce the number of sensor units, with each column representing spectral information equivalent to one sensor unit. Advantage can also be taken of the opportunity to develop statistics regarding the precise location of the edge of the canopy and the texture of the field of view with such numerical methods as fast Fourier transforms, convolution, and other recognition methods including statistical process control techniques such as mean and standard deviation control chart theory. With a multiplicity of elements, or an area array in which each column represents the spectral reflectivity of a point on a line across the crop row, repeated samples, taken in time as the motion of the unit continues through the field, spectral image data is generated and digital filtering methods can be applied to get an image of the desired object, weed or other plant or feature. Another alternative would be to utilize a previously memorized spectral distribution in the form a memory or data card to set up the unit and to establish the initial electronic memory or finger print rather than using an actual plant. Illustrative of further alternatives is the use of digital filtering and transforms which can be used to enhance recognition capability.

An alternative embodiment of the scanning and sensing unit 20 is depicted in FIG. 7. This improved alternative 120 includes an aiming or target light to facilitate identification of the plant or object which is being scanned. This unit includes a housing 122 which houses two lenses 140 and 142 that are positioned equidistant from an aperture plate 125. Affixed to the housing 120 in any conventional manner is a light source 124 that is focused upon a plant 80. Light reflected from the plant passes into the housing 122 through the lens 140, the aperture plate 125 and the second lens 142 to the diffraction grating 130. Segments of this reflected light are diffracted upon the sensor array 132 which is offset from the housing 122. In operation, this unit works in a manner similar to that of scanning and sensing unit 20.

In addition, however, a Target Light is mounted to the right of the housing 130, as viewed in the drawing. This light source, when activated, transmits light in the opposite direction of the reflected light, i.e., it passes into the housing 122, through lens 142, aperture plate 125, lens 140 where it is focused on a part of the plant 80. When the Target Light source is activated in any conventional manner, the focused light will be apparent on the same portion of the plant as the light would be reflected from lamp 124. Accordingly, when activated, the target light source will identify the actual target of the scanning and sensing unit 120. Importantly, this target light will inform the user whether the spectral sample is of the plant leaf, stem, flower etc.

Preferably, the Target Light and the lamp 124 will not be actuated at the same time.

Those skilled in the art will appreciate that the focal point of the target light and its distance from the housing will be dependent on the selection of the lens 140 and 142 and their placement within the housing.

The Plant Condition Identifier and Transmitter

Figure 6:
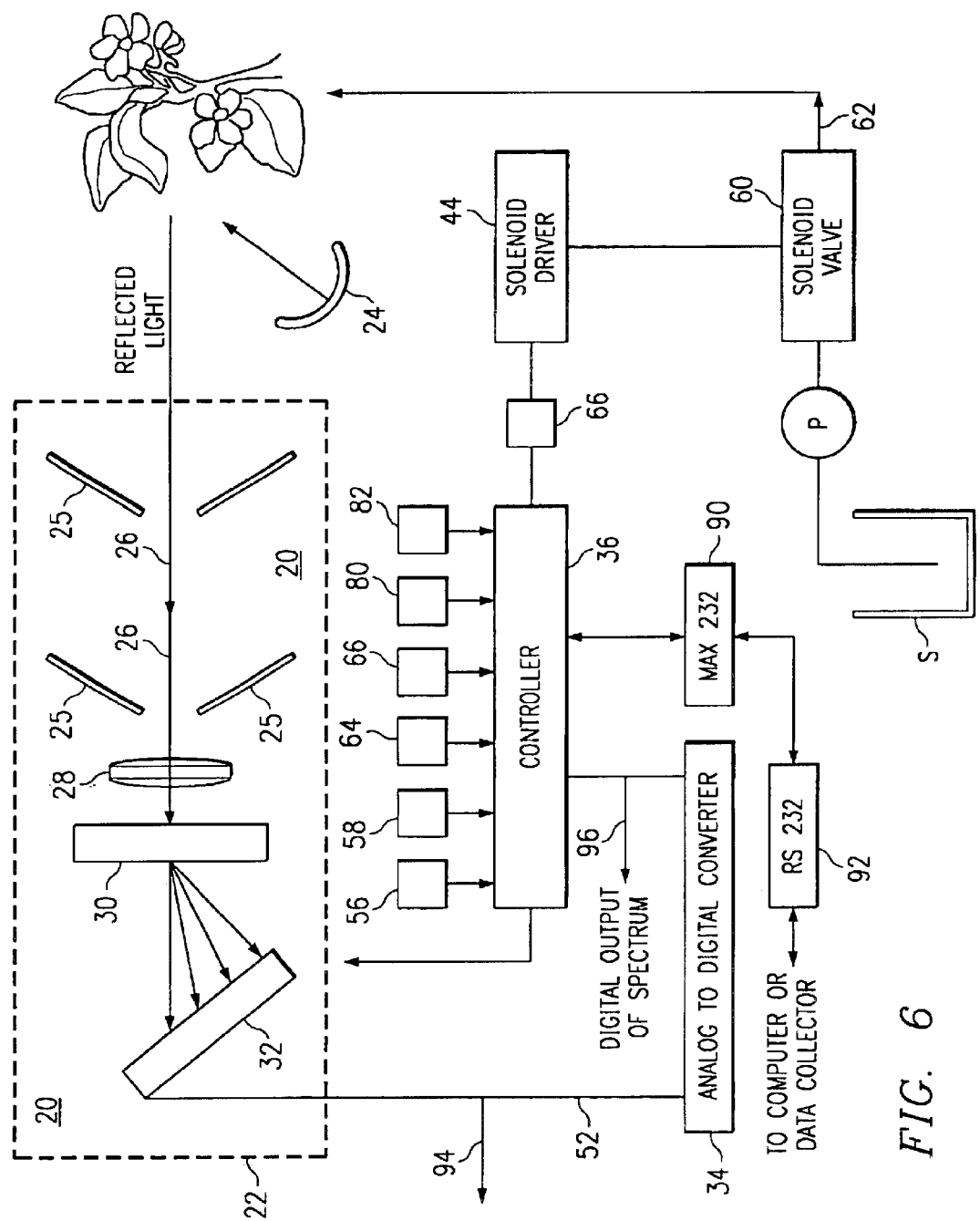
FIG. 6 is block diagram depicting additional components of a preferred embodiment of the plant identifier invention together with alternatives for transmitting the plant's spectral reflectivity, the plant's identity and its condition to a remote data collector such as computer.
Figure 6A:
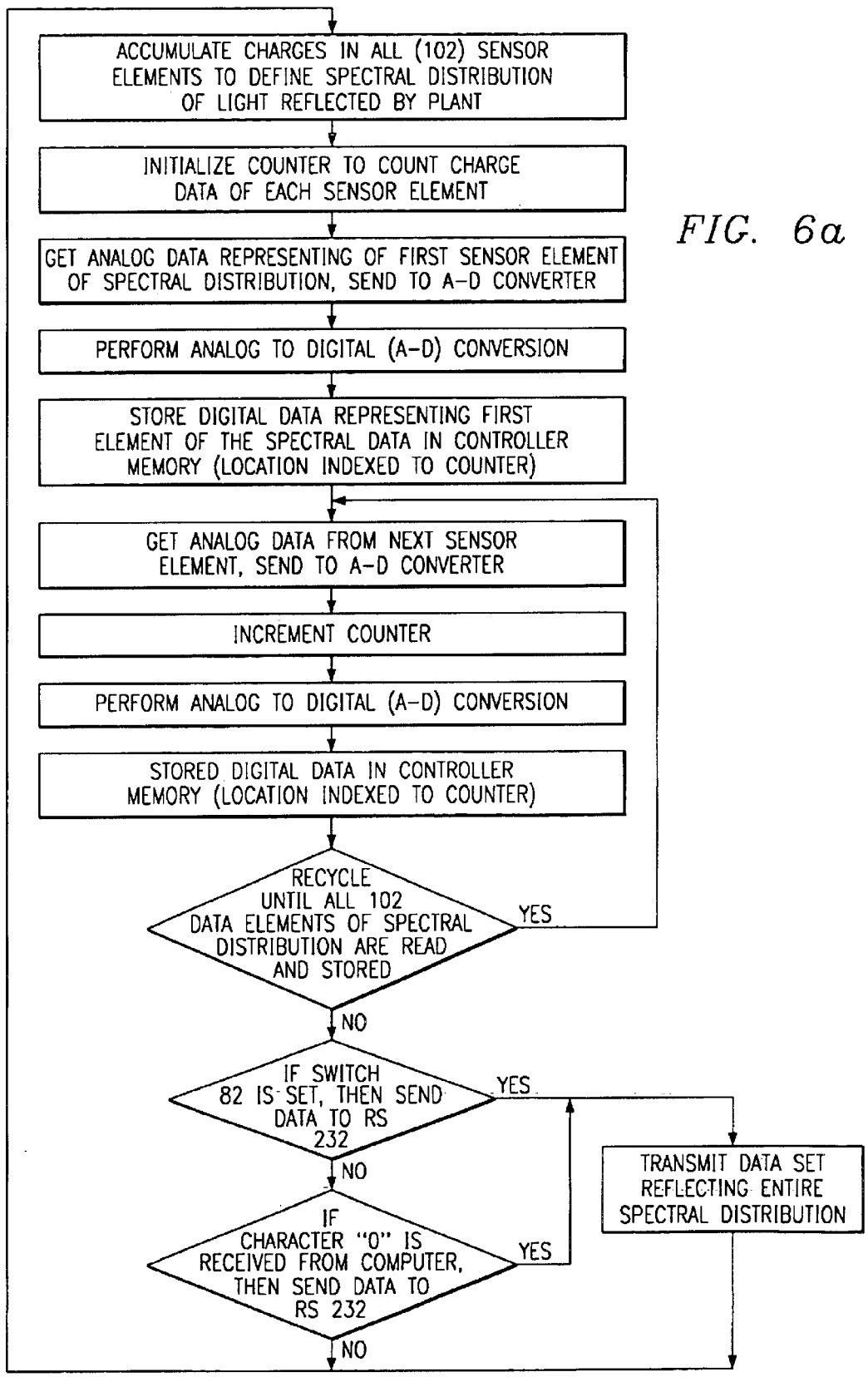
FIG. 6(a) is a flow chart disclosing additional functions of the software program to enable the microprocessor to collect and transmit data reflecting the plant's color spectrum for the purpose of identifying its species or its condition.

Another embodiment of the invention is depicted in FIG. 6. This embodiment depicts additional components for and methods of using the digital identifier to collect and transmit plant fingerprints or wide spectrum data points of plant or tissue immediate evaluation or for accumulation and subsequent analysis of the object.

In this embodiment, a toggle switch 80 is used to switch the controller program from one of plant identification to one of plant analysis, i.e., to the accumulation of a fingerprint or wide spectrum data point collection and its transmittal to an oscilloscope, computer or to a memory device for analysis. Alternatively, the data can be communicated to a portable computer physically connected to the device for plant condition analysis.

Physically, this embodiment is physically similar to the plant identification embodiment in that most of the same components are utilized. In addition, this embodiment has the mode switch 80 to activate the transmittal program routine and a send or transmit switch 82. When activated the transmit switch 82 instructs the processor 36 to serially transmit the entire full spectrum of the plant's condition to a RS 232 port 92 which may be connected to a portable computer or a radio transmitter or a digital cellular device. In addition, the processor 36 may be programmed to receive a signal, such as character "0" from the computer and to serially transmit the entire full spectrum of the plant sample to the computer where it may be stored for later analysis.

In operation of this embodiment, a program is written to reflect the software functions set forth in FIG. 6(*b*) which is then stored in program memory of the processor 36. When the mode switch 80 is activated, the light sensor accumulates a voltage charge in each of the pixels to reflect the spectral distribution of the light reflected by the plant. Such charges are sequentially sent to the analog to digital converter 34 and then transmitted to data storage memory locations within the processor 36. Preferably sample distributions are continuously taken, converted and stored for possible transmission to a memory device through the RS 232 port.

The data is transmitted upon activation of the switch 82 or upon a reception from the computer or cellular device connected to the RS 232 element 92. In addition and as an alternative to the use of the processor 36 to effect this transmission function, one may obtain the analog output from the sensor array 32 by a direct connection at 94 to the output of the sensor 32. Such a connection has been helpful in directly connecting the unit to an oscilloscope (not shown) to visually examine the spectral distribution of the light reflected by the plant. If desired, a digital oscilloscope could be used to convert the analog information to digital for further use and analysis by external means. In addition, a parallel connection 96 could be taken from the A to D converter 34 and directed to an I/O card of a computer or other device.

Another modification to this embodiment is the use of a larger linear or area array. Preferably model TSL 1401 or Texas Instruments, Inc. would be utilized because it has 128 pixels which can be utilized to obtain a more definitive fingerprint of the plant for analysis purposes. Significantly such may be most helpful in ascertaining the degree of stress or other conditions of the plant. In the event such a sensor is utilized, it will also be desirable to use an enhanced processor such as DSP Model No. TMS320F240 previously mentioned.

Like the machine code program previously set forth in this application for the plant identification routine, persons skilled in the art can easily formulate the collection and transmittal program or routine for use in conjunction with either the single sample switch 82 or the continuous mode switch 80.

In application, it is intended that the entire identification and transmittal units be incorporated into a light weight hand held case to enable plant inspectors to carry the units to the field, obtain spectral distributions of one or more plants or any part there of and to transmit such distributions to a memory device for subsequent analysis of the plant's condition. Alternatively, such a unit could also be mounted on tool bars which are carried down the row with a computer or controller transmitting the character "0" to the unit to effect transmittal or downloading of one or more sample spectral distributions of the plants or crops at various points.

In implementing these inventions, those skilled in the art will also appreciate that the spectrometer or scanning and sensing unit 20 of my invention may be calibrated. However, calibration may impose additional costs. On belief, most if not all commercial spectrometers are calibrated. However, an alternative is to avoid calibration and to approximately align a segment of light rays, for example visible red light with, for example, the center pixel of the sensor array 32. Such should always be sufficient when the same spectral identifier unit is being used for the sample and for the other objects of the population. This, for the reason that the same instrument will always diffract the same wavelengths to the same pixels and the resulting comparison will always be comparing the output of each wavelength of the sample with the output of the same wavelength of the next object of the population.

However, when different instruments using an uncalibrated sensor and scanning unit of my invention are used to generate the finger prints of objects or tissue, it may be advantageous to insure that the digital identifier or comparator 36 or computer properly compares data points generated by one scanning unit 20 with the appropriate data points generated by another sensing and scanning unit 20. For example, the magnitude of the voltage generated by a diffracted wave length segment of one sensing and scanning unit 20 should be compared and correlated with the magnitude of the voltage generated by the same wave length segment on the other sensing and scanning unit 20. Such would inherently result when using calibrated scanning and sensing units. However, if one does not desire to use calibrated units or if one does not use the same identifier unit to compare the fingerprints, it may be desirable to develop software that will modify the wave length data points of the fingerprints of one identifier to match the corresponding wave length data points of fingerprints of other identifiers. Such modifications would require software shifting of the data points to insure that similar or identical sets of wavelengths are shifted to a fixed standard for all manufactured units. Preferably, such software would be incorporated into the memory of each of the digital identifiers 36 at the time of manufacture and such would be a low cost form of calibration. Alternatively, such software may be developed for a computer receiving transmitted fingerprints for analysis.

Those skilled in the various arts will also appreciate that the present inventions have broad uses in other agricultural operations. For example, they might be used to identify specific soils on a farm to selectively apply certain fertilizers to soils having certain colors. It may well be used to identify and sort vegetables, fruits and other products by color and ripeness. Similarly, the invention may well find applicability in numerous industrial, medical and biological applications of collecting, identifying or processing products and objects including fluids and animal tissue by color. Such uses may include the early detection of skin cancers. Another diverse application would relate to color bar coding in which this invention would facilitate the encoding and reading of far more information that the present black and white bar coding. Other uses and modifications of this invention such as these will be apparent to those of ordinary skill in the art from the contents of this application.

I claim:

1. A high speed, low cost, wide spectrum plant identifier apparatus adapted to be mounted on a farm vehicle for selectively identifying plants within a field by species and for selectively applying chemicals thereto for the purposes of reducing the chemical costs and the excessive chemical application which may otherwise result in pollution problems, said apparatus comprising:

a) a sensing device for receiving reflected light from a plant, said device including a diffraction element for separating the reflected light into segments of different wavelengths and a linear sensor array having elements positioned to receive the segments and to measure the relative magnitude of such segments to define a wide spectral distribution of the plant;

b) a digital identifier connected to said sensing device and having a memory for memorizing a spectral distribution of light representing a first plant species from the field, and additional memory for receiving a spectral distributions of other plants from the field and programmable logic circuitry;

c) said logic circuitry having a program to compare the reflected spectral distribution of other plants with the memorized spectral distribution of the first species and to provide an output indicating substantial similarity between the distributions for effecting selective application of chemicals to the plants of the first species as the associated farm vehicle traverses a field.

2. An apparatus as recited in claim 1 in which said identifier comprises Digital Signal Processor.

3. An apparatus as recited in claim 1 in which said program includes the routine of making a regression analysis to determine the similarity between a first plant species and the other plants.

4. An apparatus as recited in claim 1 in which the logic circuitry includes a switch for modifying the degree of similarity to be detected between the spectral distributions.

5. A low cost, high speed spectral sensing method for collecting and wirelessly transmitting spectral information on the physical condition of an object in need of remote analysis of the condition and/or identity of the objects, said method comprising the steps of:
 a) sensing the spectral distribution of a plurality of segments of wave lengths of light reflected by the object in need of remote analysis with a portable spectral apparatus;
 b) electronically measuring the magnitude of the segments of the reflected wavelengths to define a wide spectral distribution of light received from said object;
 c) wirelessly transmitting the spectral distribution to a remote readable electronic memory to facilitate said remote analysis of the object, and
 d) said portable spectral apparatus having a target light means for aiming the apparatus at the object from which the light is to be reflected.

6. The method recited in claim 5 in which the spectral distribution is first converted to digital information prior to transmitting.

7. A high speed, low cost apparatus for selectively identifying objects, including fluids and tissue, and their condition, from within a population; said apparatus comprising:
 a) a sensing device for receiving reflected light from a sample object from the population, said device including a lens and diffraction device for separating the reflected light into a plurality of segments of wavelengths and for measuring the magnitude of the segments of reflected light to define a spectral distribution;
 b) a digital identifier connected to said sensing device and having a memory for receiving and storing a spectral distribution of light representing the sample object from said population;
 c) said digital identifier also having a memory for receiving and storing sequential spectral distributions from additional objects of the population;
 d) said digital identifier having a low cost chip with logic circuitry specially programmed to compare the subsequent spectral distribution with the memorized spectral distribution and to provide an output indicating similarity between the distributions.

8. An apparatus as recited in claim 7 in which said chip comprises a digital signal processor.

9. A low cost, digital identifier apparatus for identifying similarities of spectral distributions of two objects, said apparatus comprising:
 a) a micro controller;
 b) said micro controller having electronic memory elements for receiving digital signals reflecting a first wide spectral distribution of light segments reflected from an object;
 c) electronic memory elements for receiving digital signals reflecting spectral distribution of light segments from other objects; and
 d) logic circuitry including memory containing instructions for a regression analysis program for enabling said micro controller to compare the first spectral distribution of light segments with the spectral distribution of another object and for generating an output signal reflecting the results of said comparison.

10. An identifier apparatus as recited in claim 9 in which said micro controller and said logic circuitry comprise a Digital Signal Processor.

11. In an apparatus as recited in claim 9 in which said micro controller processor can be programmed to generate an output signal upon calculation of different coefficients of correlation.

12. A low cost, high speed method for facilitating evaluation of selected objects, said method comprising the steps of:
 a) obtaining a spectral distribution of reflected light segments from at least one sample object of a population and converting same to electronic memory;
 b) sequentially generating a spectral distribution of additional objects of a population and converting same to electronic memory;
 c) comparing said spectral distribution of the additional objects with the distribution of said sample object with a low cost electronic controller chip programmed with at least one correlation algorithm and coupled to said memories to achieve said low cost method and to produce an output signal of the similarity of said distributions.

13. A method as recited in claim 12 in which the coefficient of correlation can be varied to provide an output signal for different degrees of similarity.

14. A method as recited in claim 12 in which the degree of similarity required to generate the output signal can be increased or decreased.

15. A lightweight, portable device for collecting spectral information on agricultural plants in need of remote analysis and for electronically transmitting the information for remote analysis, said device comprising:
 a) a housing having an opening for receiving reflected light from said agricultural plant in need of said remote analysis,
 b) a diffraction device for receiving said light and for diffracting said light into a plurality of segments having different wavelengths,
 c) an array means carried by the housing and aligned for receiving a plurality of spectral segments of light having different wavelengths and to generate voltages whose magnitude generally correlates to the intensity of said segments to define a spectral fingerprint; and, d) a controller means associated with said array for transmitting the spectral fingerprint to an electronic memory for said analysis of the agricultural plant.

16. An apparatus as recited in claim 15 in which said portable device has a target light means for aiming the apparatus at the agricultural plants.

17. An apparatus as recited in claim 15 in which said controller means comprises a digital signal processor.

18. A low cost, lightweight, sensing method for obtaining spectral information on the identity and/or physical condition of objects such as plants, fluids and/or tissue for subsequent analysis of their identity and/or physical condition, comprising the steps of:
 a) sensing the spectral distribution of a plurality of wave lengths of light by segment reflected by the objects;
 b) electronically measuring the magnitude of the segments of the reflected wave lengths to define a spectrum distribution of light received from said objects; and c) wirelessly transmitting said spectral information to a readable electronic memory for said subsequent analysis and/or identification of said objects; and d) said spectral distribution being sensed by a portable spectral apparatus having a target light for aiming the apparatus at said object.

19. A method as recited in claim 18 in which said spectral distribution comprises at least 3 data points.

20. A low cost method for comparing selected objects, said method comprising the steps of:

a) obtaining a spectral distribution of reflected light segments from a representative of a sample species of a population;

b) sequentially generating a spectral distribution of additional species of a population;

c) comparing said spectral distribution of the additional species with the distribution of said representative with an electronic controller chip having an arithmetic logic unit specially programmed with a comparative algorithm to obtain said low cost method and producing an output signal when said distributions are substantially similar.

21. A method as recited in claim 20 in which said spectral distributions comprises at least three data points.

22. A method as recited in claim 20 in which said spectral distributions are compared by a mathematical algorithm.

23. A low cost apparatus for selectively identifying objects, including fluids and tissue, and their condition, from within a population; said apparatus comprising:

a) a sensing device for receiving reflected light from objects of a population, said device including a lens and diffraction device for separating the reflected light into a plurality of segments of wavelengths and for directing said segments upon an array for measuring the magnitude of the segments of reflected light to define a spectral distribution;

b) a digital identifier connected to said sensing device and having a memory for receiving and storing a spectral distribution of light representing a sample object from said population;

c) said digital identifier also having a memory for receiving and storing sequential spectral distributions from various objects of the population;

d) said digital identifier having logic circuitry programmed to compare the subsequent spectral distribution with the memorized spectral distribution and to provide an output indicating the results of the comparison of the distributions.

24. An apparatus as recited in claim 23 in which said sensing device is calibrated such that the same segments of diffracted light wavelengths are repeatedly separated and diffracted upon substantially the same area of the array.

25. An apparatus as recited in claim 23 in which said sensing device is aligned such that at least one segment of wavelengths of light is always diffracted upon the same area of the array.

26. An apparatus as recited in claim 23 in which said spectral distribution comprises at least three data points.

27. An apparatus as recited in claim 23 in which said logic circuitry comprises a digital signal processor.

28. A wide spectrum image device comprising;

a) a housing receiving light from an object and having a diffraction device for separating the light into segments of different wave lengths;

b) a linear array positioned adjacent said housing for receiving the separated wavelength segments and for electronically recording the magnitude thereof as an image; and c) an aiming device having a beam of light supported by the housing for pointing the housing towards the object from which the light is to be reflected.

29. A wide spectrum image device as recited in claim 28 which includes an electronic identifier receiving the electronically recorded image from the array and for identifying at least one property of the object.

30. A wide spectrum image device as recited in claim 29 in which said identifier comprises a digital signal processor that includes an A to D converter for converting the magnitude of the separated wave lengths to digital information.

31. A wide spectrum image device as recited in claim 29 in which said identifier is a micro processor programmed to run a regression analysis to determine the similarity between a first image and a second image.

32. An image apparatus for selectively identifying objects, including fluids and tissue, and their condition, from within a population; said apparatus comprising:

a) a sensing device for receiving reflected light from an object of a population, said device including a diffraction element for separating the reflected light into a plurality of segments of wavelengths and an array receiving said reflected light for measuring the magnitude of the segments of reflected light to obtain a spectral distribution;

b) a digital identifier connected to said sensing device and having a memory for receiving and storing a spectral distribution of light representing the sample object from said population;

c) said digital identifier also having a memory for receiving and storing sequential spectral distribution from an additional object of the population;

d) said digital identifier having logic circuitry programmed to compare the subsequent spectral distribution of the object with the spectral distribution of the sample object and to provide an output indicating similarity between the distributions; and e) an aiming light source for generating a beam of light to focus the digital identifier upon the desired target.

33. An apparatus as recited in claim 32 in which said identifier comprises a digital signal processor.

34. A low cost digital identifier apparatus for comparing spectral distributions, said device comprising:

a) electronic memory elements for receiving signals reflecting a first spectral distribution of reflected light segments;

b) electronic memory elements for receiving signals reflecting an additional spectral distribution of reflected light segments; and c) logic circuitry in which said low cost apparatus comprises a controller chip with an arithmatic logic unit interconnected with said memory elements and containing an algorithm for a regression analysis for comparing the first spectral distribution of light segments with the additional spectral distribution of reflected light segments.

35. A digital identifier apparatus as recited in claim 34 in which said controller chip and said memory elements comprises a Digital Signal Processor.

36. A digital identifier apparatus as recited in claim 34 in which the apparatus has means for changing the coefficient of correlation of said regression algorithm.

37. A digital identifier apparatus as recited in claim 34 in which the first spectral distribution is obtained from a data base.

38. A digital identifier apparatus as recited in claim 34 in which the algorithm indicates the degree of dissimilarity between the two distributions.

39. A low cost method for comparing selected objects, said method comprising the steps of:
   a) generating a spectral distribution of reflected light segments in binary form from a first object;
   b) sequentially generating a spectral distribution of reflected light segments in binary form of an additional object;
   c) electronically comparing said spectral distribution of the additional object with the distribution of said first object using a low cost chip containing an arithmatic logic unit having an algorithm.

40. A method as recited in claim 39 in which said chip comprises a micro controller and said algorithm includes a regression analysis.

41. A method as recited in claim 39 in which said light segments in numerical form are generated by directing said light upon an array whose output is converted to a digital output for comparison.

42. A method as recited in claim 41 in which said light segments are directed upon said array by a lens.

43. A low cost sensing device for objects, said device comprising:
   a) an array for receiving reflected light from objects and for generating a plurality of signals indicating the intensity of the reflected light;
   b) a comparator connected to said array for receiving signals from said array, said comparator having a regression algorithm for comparing the signals from the object with signals from a standard and for identifying the similarity between objects.

44. A device as recited in claim 43 the correlation coefficient of the regression analysis can be changed to ascertain different degrees of similarity between the object and the standard.

45. A device as recited in claim 43 the correlation coefficient of the regression analysis can be changed by a manual switch to ascertain different degrees of certainty of identification.

* * * * *